(12) United States Patent
Ardila et al.

(10) Patent No.: US 12,271,443 B1
(45) Date of Patent: Apr. 8, 2025

(54) AUTOMATIC DATA CURATION

(71) Applicant: Scale AI, Inc., San Francisco, CA (US)

(72) Inventors: Diego Ardila, Oakland, CA (US);
Russell Kaplan, San Francisco, CA (US); Vinjai Saraj Vale, Exeter, NH (US); Jihan Yin, San Francisco, CA (US)

(73) Assignee: SCALE AI, INC., San Francisco, CA (US)

( * ) Notice: Subject to any disclaimer, the term of this patent is extended or adjusted under 35 U.S.C. 154(b) by 75 days.

(21) Appl. No.: 17/482,860

(22) Filed: Sep. 23, 2021

(51) Int. Cl.
*G06F 18/214* (2023.01)
*G06F 18/21* (2023.01)
(Continued)

(52) U.S. Cl.
CPC ........ *G06F 18/2148* (2023.01); *G06F 18/214* (2023.01); *G06F 18/2155* (2023.01);
(Continued)

(58) Field of Classification Search
CPC ............ G06N 20/00; G06N 3/08; G06N 3/09; G06N 5/04; G06N 5/046; G06N 3/088; G06N 5/045; G06N 3/0895; G06N 3/091; G06N 3/02; G06V 10/82; G06V 10/70; G06V 20/70; G06V 10/7788; G06V 10/7784; G06V 10/7792; G06V 10/761; G06V 10/454; G06V 10/72; G06V 10/774; G06V 10/7753; G06V 10/778; G06T 2207/20081; G06T 2207/20084; G06T 2219/004; G06T 5/60; G06T 9/002; G16B 40/20; G16B 40/30; G06F 16/217; G06F 30/27; G06F 18/214; G06F 18/2155; G06F 18/2178; G06F 18/2185; G06F 18/217; G06F 16/215; G06F 16/2455;
(Continued)

(56) References Cited

U.S. PATENT DOCUMENTS 9,691,027 B1 * 6/2017 Sawant .............. G06F 21/6245
2008/0103996 A1 * 5/2008 Forman .................. G06N 20/00
706/12

(Continued)

OTHER PUBLICATIONS

Moller et al., ALMI—A Generic Active Learning System for Computational Object Classification in Marine Observation Images, Feb. 6, 2021 [retrieved Dec. 3, 2024], Sensors 2021, vol. 21, 16 pages. https://doi.org/10.3390/s21041134 (Year: 2021).*

*Primary Examiner* — Henok Shiferaw
*Assistant Examiner* — Dennis Rosario
(74) *Attorney, Agent, or Firm* — Squire Patton Boggs, LLP; Sarah Mirza

(57) ABSTRACT

One embodiment of the present invention sets forth a technique for curating a data sample set. The technique includes determining one or more data sampling criteria based on a sampling objective for a data sample set associated with the machine learning model. The technique also includes selecting, from a set of unlabeled data samples, at least one data sample to be labeled and added to a data sample set associated with the machine learning model based on the one or more data sampling criteria. The technique also includes, for each selected data sample, supplementing the data sample set with the selected data sample and at least one association with a label.

15 Claims, 6 Drawing Sheets

(51) Int. Cl.
  *G06N 3/088* (2023.01)
  *G06N 3/0895* (2023.01)
  *G06N 3/09* (2023.01)
  *G06N 20/00* (2019.01)
  *G06V 10/70* (2022.01)
  *G16B 40/20* (2019.01)
  *G16B 40/30* (2019.01)
  *G06F 16/24* (2019.01)
  *G06F 16/28* (2019.01)
  *G06F 16/332* (2019.01)
  *G06F 16/3329* (2025.01)
  *G06F 16/35* (2019.01)
  *G06F 16/903* (2019.01)
  *G06F 16/9032* (2019.01)
  *G06F 16/906* (2019.01)
  *G06F 18/23* (2023.01)
  *G06N 3/091* (2023.01)
  *G06V 10/82* (2022.01)

(52) U.S. Cl.
  CPC ......... *G06F 18/2193* (2023.01); *G06N 3/088* (2013.01); *G06N 3/0895* (2023.01); *G06N 3/09* (2023.01); *G06N 20/00* (2019.01); *G06V 10/70* (2022.01); *G16B 40/20* (2019.02); *G16B 40/30* (2019.02); *G06F 16/24* (2019.01); *G06F 16/285* (2019.01); *G06F 16/3329* (2019.01); *G06F 16/35* (2019.01); *G06F 16/903* (2019.01); *G06F 16/90332* (2019.01); *G06F 16/906* (2019.01); *G06F 18/217* (2023.01); *G06F 18/23* (2023.01); *G06N 3/091* (2023.01); *G06V 10/82* (2022.01)

(58) Field of Classification Search
  CPC .. G06F 16/248; G06F 16/9035; G06F 16/906; G06F 16/90335; G06F 16/285; G06F 16/33; G06F 16/335; G06F 16/355; G06F 16/953; G06F 18/23213; G06F 18/23; G06F 16/2457; G06F 16/24573; G06F 16/287; G06F 16/337; G06F 16/3329; G06F 16/3331; G06F 16/35; G06F 18/2193; G06F 16/242; G06F 16/24; G06F 16/2458; G06F 16/245; G06F 16/903; G06F 16/90332; G06F 18/2148
  See application file for complete search history.

(56) References Cited

U.S. PATENT DOCUMENTS

2016/0078359 A1* 3/2016 Csurka ................ G06V 10/776 706/12
2019/0378044 A1* 12/2019 Jeffery ................ G06N 20/00

* cited by examiner

AUTOMATIC DATA CURATION

BACKGROUND

Technical Field

Embodiments of the present disclosure relate generally to supervised and semi-supervised training of machine learning models and, more specifically, to automatic data curation.

Description of the Related Art

Machine learning models are often trained on data sample sets of labeled data samples, in which each data sample is tagged with one or more labels. In some scenarios, the labels represent categories of one or more features of the data sample. For example, an image-based data sample set includes images and labels that indicate an image type, a feature of the image, such as a location or time of day, and/or a type of object present in the image, such as a type of vehicle. Trained machine learning models can analyze unlabeled data samples to predict one or more labels according to the associations between the labels and data samples in the data sample set.

The performance of a trained machine learning model depends on the size of the data sample set and the quality of the data sample set. Oftentimes, a deficiency in the number of data samples in the data sample set or inaccuracies in the data sample set leads to a poorly performing machine learning model. For example, if the data sample set has many more data samples for a first label than a second label, the machine learning model can generate predictions that are disproportionately skewed toward the first label. As another example, if the data sample set includes data samples with features that are highly correlated with and representative of the labels, the machine learning model can be overtrained and cannot generalize to predict labels for outlier data samples. As yet another example, if the data sample set includes data samples that share a feature but are differently and inconsistently labeled, the machine learning model cannot produce labels that accurately reflect the labeling inconsistencies for the feature.

In such cases, it is often desirable to supplement a data sample set with additional data samples and associated labels. A developer can review a set of unlabeled data samples to select and label some of the data samples for addition to the data sample set. However, manual selection from the set of unlabeled data samples can be time-consuming and/or expensive. For example, the unlabeled sample set can be very large, and it might take the developer a long time to review the unlabeled sample set to determine which unlabeled data samples to label in order to address the limitations of the data sample set. Instead, data samples can be selected automatically from an unlabeled data sample set, such as a random selection from the set of unlabeled data samples, or based on time (e.g., selecting the oldest or newest unlabeled data samples first), for presentation to and labeling by a developer.

One drawback of the above technique is that the supplemented data sample set fails to improve the performance of trained or retrained machine learning models in comparison with machine learning models trained on the initial or original data sample set. As a first example, the developer or a random selection process might select, from the unlabeled data sample set, data samples for which a selected label is already overrepresented in the data sample set. As a result, the overrepresentation of the label and underrepresentation of other labels are exacerbated. As a second example, the developer might not fully or correctly understand the causes of poor performance of trained machine learning models. For instance, the training data might have few data samples that are not well-correlated labels (e.g., outliers that are not closely correlated with any of the labels). However, the developer or a random process might supplement the data sample set with additional data samples that are highly correlated with and representative of the labels. As a result, trained or retrained machine learning models cannot generalize the key features of each label in order to predict labels correctly outlier data samples, and instead overtrain on the highly correlated data samples. In these and other cases, despite requiring additional developer time for selecting and labeling the unlabeled data samples and additional time to train machine learning models, the supplemented data sample set fails to improve the performance of trained machine learning models.

As the foregoing illustrates, what is needed in the art are techniques for automatic data curation.

SUMMARY

In some embodiments, a computer-implemented method for curating a data sample set includes determining one or more data sampling criteria based on a sampling objective for the data sample set associated with the machine learning model. The computer-implemented method also includes selecting, from a set of unlabeled data samples, at least one data sample to be labeled and added to the data sample set based on the one or more data sampling criteria. The computer-implemented method also includes, for each selected data sample, supplementing the data sample set with the selected data sample and at least one association with a label.

In some embodiments, one or more non-transitory computer readable media stores instructions that, when executed by one or more processors, cause the one or more processors to perform the step of determining one or more data sampling criteria based on a sampling objective for a data sample set associated with a machine learning model. The instructions further cause the one or more processors to perform the step of selecting, from a set of unlabeled data samples, at least one data sample to be labeled and added to the data sample set based on the one or more data sampling criteria. The instructions further cause the one or more processors to perform the step of, for each selected data sample, supplementing the data sample set with the selected data sample and at least one association with a label.

In some embodiments, a system includes a memory that stores instructions, and a processor that is coupled to the memory and, when executing the instructions, is configured to determine one or more data sampling criteria based on a sampling objective for a data sample set associated with a machine learning model. The instructions further configure the processor to select, from a set of unlabeled data samples, at least one data sample to be labeled and added to the data sample set based on the one or more data sampling criteria. The instructions further configure the processor to, for each selected data sample, supplement the data sample set with the selected data sample and at least one association with a label.

At least one technical advantage of the disclosed techniques is the data sample set is supplemented to include additional data samples that can improve the performance of machine learning models training on the supplemented data sample set, such as (without limitation) improving label balance, improving robustness, and/or improving consistency. Machine learning models that are trained or retrained on the supplemented data sample set can exhibit improved performance such as labeling accuracy, precision, and/or recall. Further, supplementing the data sample set with data samples based on an indicated set of objectives for improving machine learning models can increase the likelihood of successful training while reducing cost and complexity. Finally, allowing a developer to indicate objectives for improved machine learning models, and selecting unlabeled data samples for labeling based on the indicated objectives, can increase the performance of machine learning models trained on the supplemented data sample set even if the developer does not understand the causes of poor performance.

BRIEF DESCRIPTION OF THE DRAWINGS

So that the manner in which the above recited features of the various embodiments can be understood in detail, a more particular description of the inventive concepts, briefly summarized above, may be had by reference to various embodiments. some of which are illustrated in the appended drawings. It is to be noted, however, that the appended drawings illustrate only typical embodiments of the inventive concepts and are therefore not to be considered limiting of scope in any way, and that there are other equally effective embodiments.

DETAILED DESCRIPTION

In the following description, numerous specific details are set forth to provide a more thorough understanding of the various embodiments. However, it will be apparent to one of skilled in the art that the inventive concepts may be practiced without one or more of these specific details.

Figure 1:
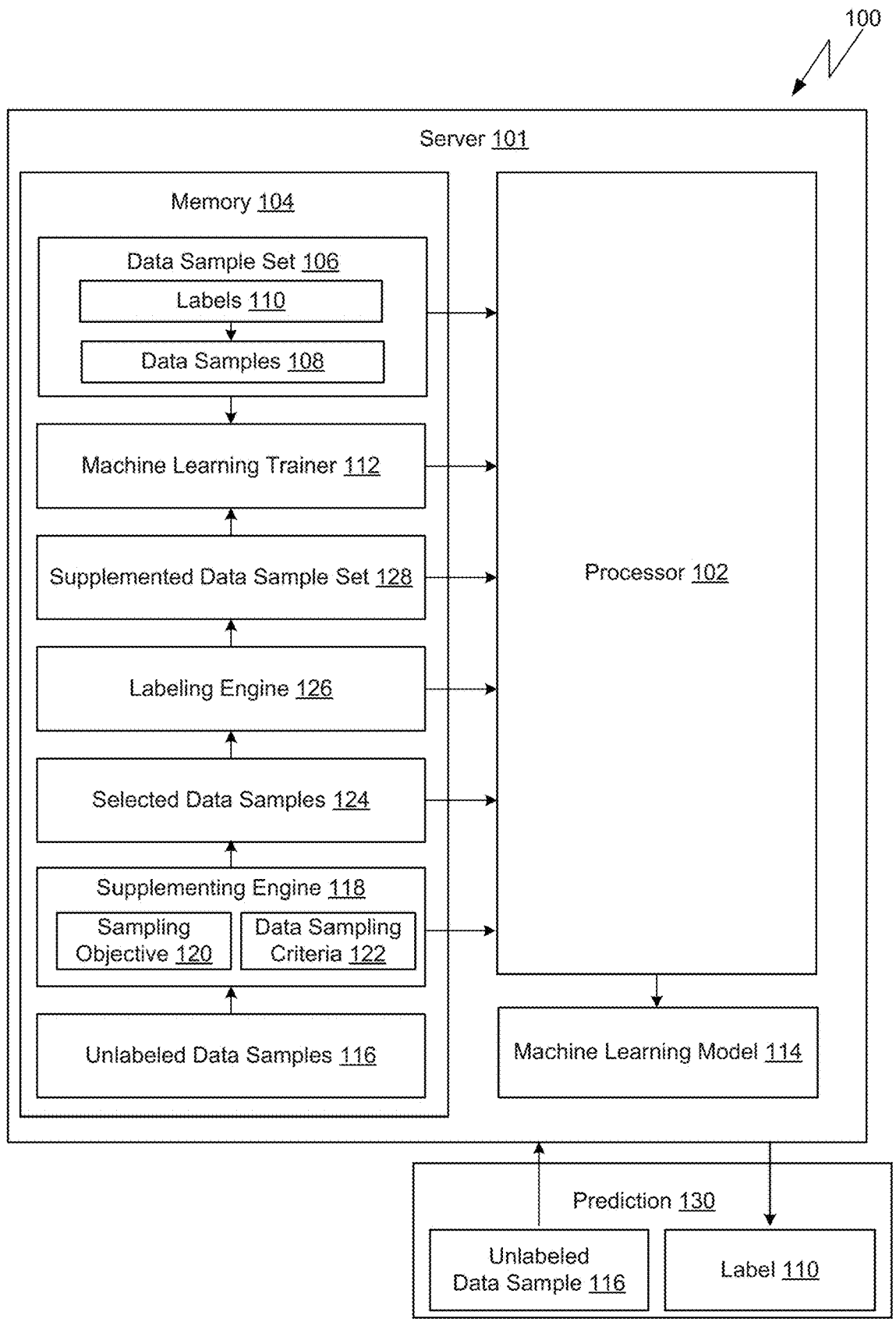
FIG. 1 is a system configured to implement one or more embodiments.

FIG. 1 is a system 100 configured to implement one or more embodiments. As shown, a server 101 within system 100 includes a processor 102, a memory 104, and a machine learning model 114. The memory 104 includes a data sample set 106, including labels 110 associated with data samples 108. The memory 104 also includes a machine learning trainer 112, a set of unlabeled data samples 116, a supplementing engine 118 that selects data samples 124 from the unlabeled data samples 116, and a labeling engine 126 that determines labels 110 for the data samples selected by the supplementing engine 118.

The processor 102 executes the machine learning trainer 112 to train the machine learning model 114 using the data sample set 106. The machine learning model 114 can be an artificial neural network including a series of layers of neurons. In various embodiments, the neurons of each layer are at least partly connected to, and receive input from, an input source and/or one or more neurons of a previous layer. Each neuron can multiply each input by a weight; process a sum of the weighted inputs using an activation function; and provide an output of the activation function as the output of the artificial neural network and/or as input to a next layer of the artificial neural network. In various embodiments, the machine learning model 114 can include features such as convolutional filters that are applied by each layer to subsets of the input; memory structures, such as long short-term memory (LSTM) units or gated recurrent units (GRU); one or more encoder and/or decoder layers; or the like. Alternatively or additionally, the machine learning model 114 can include one or more other types of models, such as, without limitation, a Bayesian classifier, a Gaussian mixture model, a k-nearest-neighbor model, a decision tree or a set of decision trees such as a random forest, a restricted Boltzmann machine, or the like, or an ensemble of two or more machine learning models of the same or different types. In various embodiments, the machine learning model 114 can perform a variety of tasks, such as, without limitation, data classification or clustering, anomaly detection, computer vision (CV), natural language processing (NLP), semantic analysis, knowledge inference, system control, or the like.

As shown, the machine learning trainer 112 is a program stored in the memory 104 and executed by the processor 102 to train the machine learning model 114. The machine learning trainer 112 trains the machine learning model 114 to output predictions for data samples 108 included in the data sample set 106. The machine learning trainer 112 compares the label 110 previously associated with a data sample 108 with a label 110 predicted by the machine learning model 114. If the associated label 110 and the predicted label 110 do not match, then the machine learning trainer 112 adjusts the internal weights of the neurons of the machine learning model 114. The machine learning trainer 112 repeats this weight adjustment process over the course of training until the output of the machine learning model 114 is sufficiently close to or matches with the label 110 associated with the data sample 108. In various embodiments, in various embodiments, during training, the machine learning trainer 112 monitors a performance metric, such as a loss function, that indicates the correspondence between the associated labels 110 and the predicted labels 110 for the data samples 108 of the data sample set 106. The machine learning trainer 112 trains the machine learning model 114 through one or more epochs until the performance metric indicates that the correspondence of the associated labels 110 and the predicted labels 110 is within an acceptable range of accuracy. The trained machine learning model 114 is capable of making predictions 130 of labels 110 for unlabeled data samples 116 in a manner that is consistent with the associations of the data sample set 106.

In some embodiments, a machine learning model 114 that is trained on the data sample set 106 exhibits indicators of poor performance in one or more respects. As a first example, and without limitation, the machine learning model 114 correctly predicts a first label 110 for the data samples 108, but poorly predicts a second label 110 for the data samples 108. That is, the machine learning model 114 exhibits an imbalance in its performance for different labels 110. As a second example, and without limitation, the machine learning model 114 correctly predicts labels 110 for some data samples 108 that are very similar to one another, but does not correctly predict labels 110 for data samples 108 that are not similar to the correctly labeled data samples

108. That is, the machine learning model 114 exhibits poor robustness in the determinative features of each label 110 and is unable to generalize the characteristic features of data samples 108 that are associated with each label 110. As a third example, and without limitation, the machine learning model 114 inconsistently labels data samples 108 that are similar to one another, such as data samples 108 that are near a classification decision boundary between two labels 110.

Based on such indicators of poor performance, a developer wishes to improve the performance of the machine learning model 114. In some embodiments, the developer indicates one or more sampling objectives 120 to be achieved for a data sample set associated with the machine learning model 114, such as (without limitation) improving label balance, improving label robustness, or improving label consistency. In some other embodiments, one or more sampling objectives 120 are generated automatically, such as by evaluating performance metrics of the machine learning model 114 and identifying one or more areas of deficient performance. The sampling objectives 120 are presented to a developer, who can approve, modify, or supplement the one or more sampling objectives 120.

The supplementing engine 118 is a program stored in the memory 104 and executed by the processor 102 to facilitate the selection of unlabeled data samples 116 to be labeled and included in the supplemented data sample set 128. In particular, the supplementing engine 118 determines one or more data sampling criteria 122 based on the one or more sampling objectives 120. The one or more data sampling criteria 122 indicate properties of data samples 116 that could supplement the data sample set 106, which could improve the performance of the machine learning model 114 if trained or retrained on the supplemented data sample set 128 if supplemented according to the one or more sampling objectives 120. For example and without limitation, the properties of the data samples 108 could be based on the content of the data samples 116, such as a lightness or brightness level of an image. The properties of the data samples 116 could be based on data features determined by the machine learning model 114, such as a classification, or a feature vector generated by one or more layers of a convolutional neural network (CNN). The properties of the data samples 116 could be based on metadata, such as a date, time of day, or geocoordinate included in image EXIF metadata, or a source of the data samples 116. The properties of the data samples 116 could be based on a comparison of each unlabeled data sample 116 with one or more of the labeled data samples 108, such as a similarity measurement between the unlabeled data sample 116 and the labeled data samples 108 that are associated with a label 110.

As a first example, and without limitation, for a sampling objective 120 of improving label balance, the supplementing engine 118 determines that the data sample set 106 includes the number of data samples 108 associated with a first label 110 is disproportionate compared with the number of data samples 108 associated with a second label 110. For instance, an imbalanced data sample set 106 could include 1,000 data samples 108 associated with a first label 110 and only 50 data samples 108 associated with a second label 110. An imbalanced data sample set 106 could include a wide variety of data samples 108 associated with a first label 110 (e.g., images of 100 different types of cars associated with a "car" label 110), but a limited variety of data samples 108 associated with a second label 110 (e.g., only images of a school bus associated with a "bus" label 110). An imbalanced data sample set 106 could result in a trained machine learning model 114 with acceptable performance metrics for a first label 110 (e.g., an F1 score of 0.9 for a first label 110), and a poor performance metrics for a second label 110 (e.g., an F1 score of 0.4 for a second label 110). In such cases, the data sample set 106 overrepresents the first label 110 and underrepresents the second label 110. For instance, a data sample set of images of vehicles includes many images of cars, but few images of bicycles. In such cases, the supplementing engine 118 selects a data sampling criterion 122 for data samples 108 that could be associated with a second label 110.

As a second example, and without limitation, for a sampling objective 120 of improving label robustness, the supplementing engine 118 determines that data samples 108 of the data sample set 106 associated with each of the labels 110 are very similar to one another. Alternatively or additionally, the data sample set 106 can include data samples 108 that share a specific set of properties. For instance, a data sample set 106 of images of vehicles includes many images of trucks that are limited to semi-trailer trucks, and includes few or no images of other types of trucks, such as pickup trucks or construction trucks. In such cases, the supplementing engine 118 selects a data sampling criterion 122 for data samples 108 that could be associated with each label 110, and that are not similar to the data samples 108 that are already associated with each label 110.

As a third example, and without limitation, for a sampling objective 120 of improving label consistency, the supplementing engine 118 determines that data samples 108 associated with a first label 110 are very different than data samples associated with a second label 110. For instance, a data sample set 106 of images taken at different times of day includes many images associated with the "images at night" label 110 that are dark images taken late at night, and many images associated with the "images during the day" label 110 that are bright images taken during midday. As a result, a machine learning model 114 trained on this data sample set 106 accurately classifies images that were taken late at night or during midday. However, the machine learning model 114 inconsistently labels images taken at dusk as either taken at night or during the day. For example, the machine learning model 114 could classify a first image at dusk of a person wearing dark clothing as an "image at night." and could identify a second image at dusk of the same person wearing light clothing as an "image during the day." In such cases, the supplementing engine 118 selects a data sampling criterion 122 for data samples 108 that are dissimilar to the data samples 108 that are associated with either the "images during the day" label 110 or the "images at night" label 110. Such data samples 108 can be close to a classification decision boundary between the two labels 110.

In some cases, the supplementing engine 118 determines a plurality of data sampling criteria 122 based on a sampling objective 120, where data samples 108 satisfy each of the plurality of data sampling criteria 122 based on a particular subset of properties. For example, and without limitation, which could improve label balance, the supplementing engine 118 can determine a first sampling criterion 122 indicating data samples 108 that are similar to the data samples 108 associated with an underrepresented label 110. Concurrently, the supplementing engine 118 can determine a second sampling criterion 122 indicating data samples 108 that are dissimilar to the data samples 108 associated with an overrepresented label 110. Alternatively or additionally, in some cases, the supplementing engine 118 determines a plurality of data sampling criteria 122 based on a plurality of sampling objectives 120. For example, and without limitation, the supplementing engine 118 can determine a first sampling criterion 122 indicating data samples 108 that might be associated with an underrepresented label 110, which could improve label balance. Concurrently, the supplementing engine 118 can determine a second sampling criterion 122 indicating data samples 108 that are dissimilar to the existing data samples 108 associated with the underrepresented label 110, which could improve label robustness.

Based on the one or more data sampling criteria 122, the supplementing engine 118 selects, from a set of unlabeled data samples 116, at least one data sample 124 to be labeled. The data samples 124 that match the data sampling criteria 122 are unlabeled data samples that, if labeled and added to the data sample set 106, would improve the performance of machine learning models 144 trained on the data sample set 106 being supplemented according to the sampling objectives 120.

The labeling engine 126 is a program stored in the memory 104 and executed by the processor 102 to generate a supplemented data sample set 128 to train or retrain the machine learning model 114. In particular, the labeling engine 126 determines labels 110 to be associated with the selected data samples 124. In some embodiments, the labeling engine 126 presents each selected data sample 124 to a user (e.g., a developer), and can receive a selection of at least one label 110 to be associated with the selected data sample 124. The labeling engine 126 generates the supplemented data sample set 128, e.g., as a combination of the data sample set 106 and the labeled selected data samples 124, or as a second data sample set 106 on which the machine learning model 114 can be trained or retrained.

Based on the supplemented data sample set 128, the machine learning trainer 112 trains or retrains the machine learning model 114. In some embodiments, the machine learning model 114 continues or reinitiates the training of the machine learning model 114 using the supplemented data sample set 128, optionally including the original data sample set 106. In some embodiments, based on the supplemented data sample set 128, the machine learning model 114 reinitializes a previously trained machine learning model 114 or creates a new machine learning model 114, and initiates a new training process using the supplemented data sample set 128. The trained or retrained machine learning model 114 exhibits improved performance due to being trained on the supplemented data sample set 128 based on the sampling objectives 120.

Some embodiments of the disclosed techniques include different architectures than as shown in FIG. 1. As a first such example and without limitation, various embodiments include various types of processors 102. In various embodiments, the processor 102 includes a CPU, a GPU, a TPU, an ASIC, or the like. Some embodiments include two or more processors 102 of a same or similar type (e.g., two or more CPUs of the same or similar types). Alternatively or additionally, some embodiments include processors 102 of different types (e.g., two CPUs of different types; one or more CPUs and one or more GPUs or TPUs; or one or more CPUs and one or more FPGAs). In some embodiments, two or more processors 102 perform a part of the disclosed techniques in tandem (e.g., each CPU training the machine learning model 114 over a subset of the data sample set 106). Alternatively or additionally, in some embodiments, two or more processors 102 perform different parts of the disclosed techniques (e.g., one CPU executing the machine learning trainer 112 to train the machine learning model 114, and one CPU executing the supplementing engine 118 to generate the supplemented data sample set 128).

As a second such example and without limitation, various embodiments include various types of memory 104. Some embodiments include two or more memories 104 of a same or similar type (e.g., a Redundant Array of Disks (RAID) array). Alternatively or additionally, some embodiments include two or more memories 104 of different types (e.g., one or more hard disk drives and one or more solid-state storage devices). In some embodiments, two or more memories 104 distributively store a component (e.g., storing the data sample set 106 to span two or more memories 104). Alternatively or additionally, in some embodiments, a first memory 104 stores a first component (e.g., the data sample set 106) and a second memory 104 stores a second component (e.g., the machine learning trainer 112).

As a third such example and without limitation, some disclosed embodiments include different implementations of the machine learning trainer 112 and/or the supplementing engine 118. In some embodiments, at least part of the machine learning trainer 112 and/or the supplementing engine 118 is embodied as a program in a high-level programming language (e.g., C, Java, or Python), including a compiled product thereof. Alternatively or additionally, in some embodiments, at least part of the machine learning trainer 112 and/or the supplementing engine 118 is embodied in hardware-level instructions (e.g., a firmware that the processor 102 loads and executes). Alternatively or additionally, in some embodiments, at least part of the machine learning trainer 112 and/or the supplementing engine 118 is a configuration of a hardware circuit (e.g., configurations of the lookup tables within the logic blocks of one or more FPGAs). In some embodiments, the memory 104 includes additional components (e.g., machine learning libraries used by the machine learning trainer 112 and/or supplementing engine 118).

As a fourth such example and without limitation, instead of one server 101, some disclosed embodiments include two or more servers 101 that together apply the disclosed techniques. Some embodiments include two or more servers 101 that distributively perform one operation (e.g., a first server 101 and a second server 101 that respectively train the machine learning model 114 over different parts of the data sample set 106). Alternatively or additionally, some embodiments include two or more servers 101 that execute different parts of one operation (e.g., a first server 101 that displays a supplementing engine 118 for a user, and a second server 101 that executes the back-end operations of the supplementing engine 118). Alternatively or additionally, some embodiments include two or more servers 101 that perform different operations (e.g. a first server 101 that trains the machine learning model 114, and a second server 101 that executes the supplementing engine 118). In some embodiments, two or more servers 101 communicate through a localized connection, such as through a shared bus or a local area network. Alternatively or additionally, in some embodiments, two or more servers 101 communicate through a remote connection, such as the Internet, a virtual private network (VPN), or a public or private cloud.

In various embodiments, the labeled data samples 108 and the unlabeled data samples 116 can be various types, including without limitation, images, videos, sounds, text, sensor measurements, or the like, or any combination thereof. In some embodiments, the data sample set 106 can be the basis of a previous or current training of the machine learning model 114, and the supplementing engine 118 can generate the supplemented data sample set 128, which could improve the training or retraining of the machine learning model 114. In some embodiments, the data sample set 106 can be generated for a future training of the machine learning model 114, and based on an identified deficiency of the data sample set 106 (e.g., an underrepresented label 110), the supplementing engine 118 can generate the supplemented data sample set 128 to supplement the training of the machine learning model 114.

In various embodiments, the supplementing engine 118 determines, in various ways, one or more sampling objectives 120 used to determine the data sampling criteria 122. In some embodiments, the supplementing engine 118 receives one or more sampling objectives 120 from a user. For example and without limitation, the user might indicate a request to improve label balance, improve label robustness, and/or improve label consistency for the data sample set associated with the machine learning model 114.

In some embodiments, the supplementing engine 118 initially determines a sampling objective 120 for the data sample set 106 associated with the machine learning model 114. In some embodiments, the supplementing engine 118 determines the sampling objective 120 based on the data sample set 106. For example and without limitation, the supplementing engine 118 can determine that the data sample set 106 exhibits label imbalance (e.g., many data samples 108 for a first label 110 and few data samples 108 for a second label 110), a deficiency of label robustness (e.g., data samples 108 for a label 110 that are very similar to each other), and/or a deficiency of label consistency (e.g., two or more data samples 108 that are very similar to each other and that are associated with different labels 110).

In some embodiments, the supplementing engine 118 initially determines a sampling objective 120 for the data sample set 106 associated with the machine learning model 114 based on an analysis of the machine learning model. In particular. the supplementing engine 118 can determine the sampling objective 120 based on predictions of the machine learning model 114 for at least one data sample 108 of the data sample set 106. The predictions can include, for example, the labels 110 associated with one or more data samples 108 of the data sample set 106; bounding boxes around identified features in data samples 108; and/or prediction confidence scores of the predictions. In some embodiments, the supplementing engine 118 determines the sampling objective 120 based on a set of class probability distributions of associations between the labels 110 and at least one data sample 108. In various embodiments, the predictions can be generated during the determining of the sampling objective 120; stored during an initial training of the machine learning model 114; or received (e.g., from a user) for a machine learning model 114 to be trained or retrained. Based on the predictions, the supplementing engine 118 can determine that the machine learning model 114 produces predictions for a first label 110 that are disproportionate with the predictions of a second label 110. The supplementing engine 118 can determine that the machine learning model 114 produces class probability for which the highest probabilities of various labels 110 are often very close, possibly resulting in inconsistent labeling by the machine learning model 114.

Figure 2:
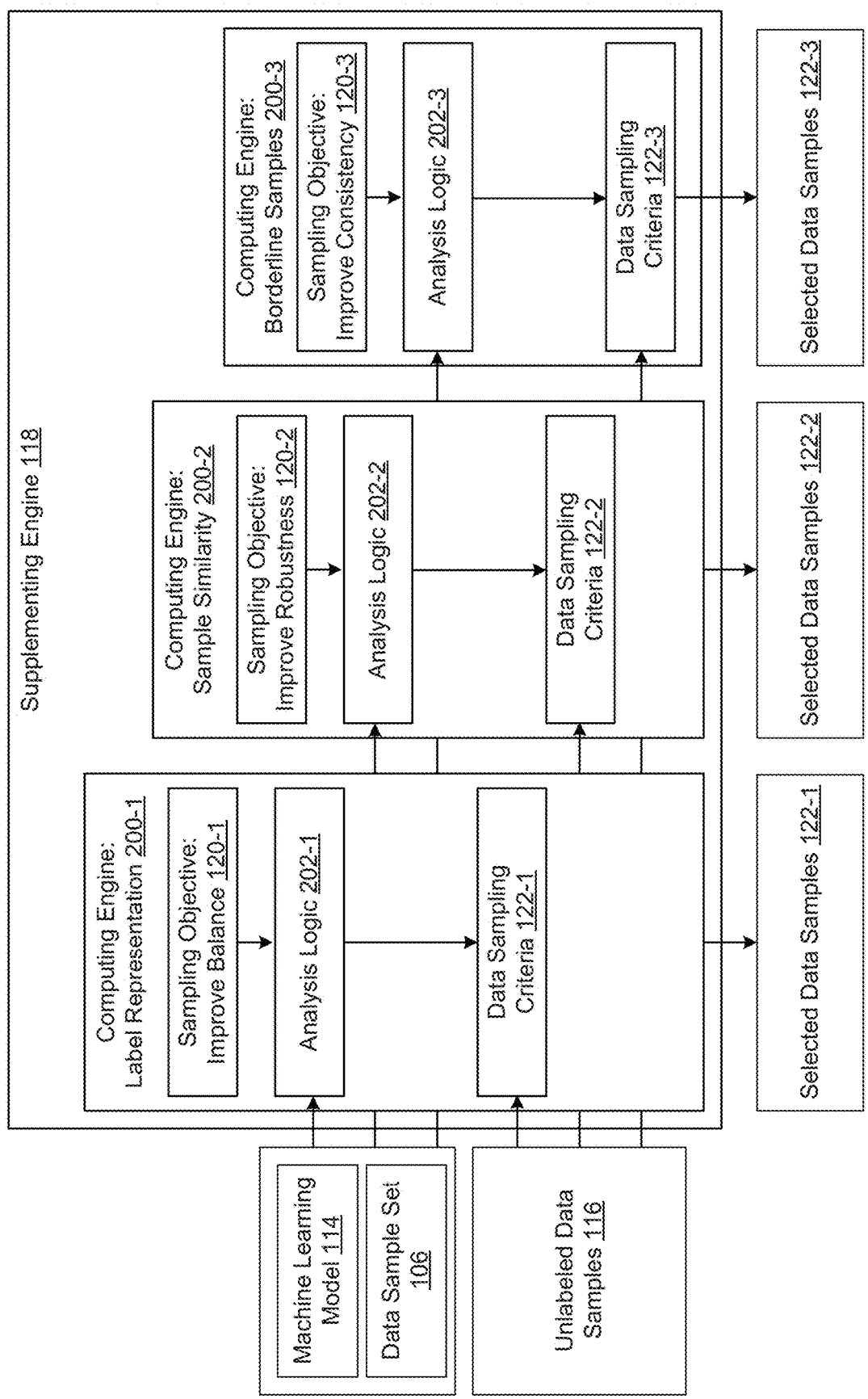
FIG. 2 is an illustration of the supplementing engine of FIG. 1, according to one or more embodiments.

FIG. 2 is an illustration of the supplementing engine 118 of FIG. 1, according to one or more embodiments. As shown, the supplementing engine 118 evaluates one or both of a data sample set 106 or a machine learning model 114 in order to select the data sampling criteria 122 that can be used to select data samples 124 from the unlabeled data samples 116 to be labeled and added to the data sample set 106.

The supplementing engine 118 selects a sampling objective from a sampling objective set. More particularly, the supplementing engine 118 includes a set of computing engines 200. For each sampling objective included in the sampling objective set, the supplementing engine 118 generates corresponding data sampling criteria via a different computing engine 200 in the set of computing engines 200. Each computing engine 200 applies an analysis logic 202 to the machine learning model 114 and/or data sample set 106 in order to determine the relevance of the sampling objective 120 of the computing engine 200.

A first computing engine 200-1 is configured to evaluate the machine learning model 114 and/or data sample set 106 to determine label representation, and the relevance of a sampling objective 120-1 of improving label balance. For example and without limitation, the first computing engine 200-1 can apply an analysis logic 202-1 to the machine learning model 114 to determine a proportionality of the label predictions (e.g., whether the machine learning model 114 disproportionately predicts a first label 110 as compared with a second label 110). Alternatively or additionally, the first computing engine 200-1 can apply the analysis logic 202-1 to the data sample set 106 to determine the representativeness of the data samples 108 (e.g., whether the data sample set 106 includes a disproportionate number of data samples 108 associated with a first label 110 as compared with a second label 110). Based on the analysis logic 202-1, the first computing engine 200-1 can generate one or more data sampling criteria 122-1 indicating properties of data samples that could be selected from the set of unlabeled data samples 116, which could improve label representation of the machine learning model 114. For example and without limitation, the one or more sampling criteria 122-1 could indicate an unlabeled data samples 116 for which the machine learning model 114 predicts a label 110 that is underrepresented in the data sample set 106.

A second computing engine 200-2 is configured to evaluate the machine learning model 114 and/or data sample set 106 to determine sample similarity, and the relevance of a sampling objective 120-2 of improving robustness. For example and without limitation, the second computing engine 200-2 can apply an analysis logic 202-2 to the machine learning model 114 to determine the similarity of feature vectors produced for the data samples (e.g., whether the machine learning model 114 produces unusually uniform or similar feature vectors for the data samples 108 associated with a particular label 110). Alternatively or additionally, the second computing engine 200-2 can apply the analysis logic 202-2 to the data sample set 106 to determine the similarity of the data samples 108 (e.g., whether the data sample set 106 includes data samples 108 for each label 110 that appear to be very similar to each other). Based on the analysis logic 202-2, the second computing engine 200-2 can generate one or more data sampling criteria 122-2 indicating properties of data samples that could be selected from the set of unlabeled data samples 116, which could improve the robustness of the machine learning model 114. For example and without limitation, the one or more data sampling criteria 122-2 could indicate unlabeled data samples 116 for which the machine learning model 114 predicts a label 110, and that are different than labeled data samples 108 that are associated with the label 110.

A third computing engine 200-3 is configured to evaluate the machine learning model 114 and/or data sample set 106 to determine sample similarity, and the relevance of a sampling objective 120-3 of improving consistency. For example and without limitation, the third computing engine 200-3 can apply an analysis logic 202-3 to the machine learning model 114 to determine the prediction of different labels for data samples with very similar feature vectors (e.g., whether slight variations in a feature vector produce different predictions of labels 110). Alternatively or additionally, the third computing engine 200-3 can apply the analysis logic 202-3 to the data sample set 106 to determine the availability of borderline data samples 108 (e.g., whether the data sample set 106 includes data samples 108 that appear to be quite similar, but have different labels 110). Based on the analysis logic 202-3, the third computing engine 200-3 can generate one or more data sampling criteria 122-3 indicating properties of data samples that could be selected from the set of unlabeled data samples 116, which could improve the consistency of the machine learning model 114. For example and without limitation, the one or more sampling criteria 122-3 could indicate unlabeled data samples 116 for which the machine learning model 114 predicts at least two labels 110 with confidence scores for which a difference is within a confidence score difference threshold.

As shown, the supplementing engine 118 includes a set of computing engines 200. In some embodiments, the supplementing engine 118 can extend or augment the set of computing engines 200 (e.g., by receiving and adding a new computing engine 200 based on a new sampling objective 120). In some embodiments, one or more of the computing engines 200 is based on a domain of the data sample set 106. For example and without limitation, if the data sample set 106 includes images and labels of objects, the set of computing engines 200 can include an image-based computing engine 200 based on a sampling objective 120 of improving the accuracy of bounding boxes detected around objects in the images. In various embodiments, the supplementing engine 188 can add a domain-specific computing engine 200 is added to the set of computing engines 200 based on a determination of the domain of the data sample set 106, and/or by receiving a domain-specific computing engine 200 provided by a user.

In some embodiments, the supplementing engine 118 determines the one or more data sampling criteria 122 by, for each sampling objective 120 of a set of sampling objectives 120, invoking a computing engine 200 configured to evaluate the sampling objective 120, and selecting the one or more data sampling criteria 122 based on the data sampling criteria 122 generated by each computing engine 200. For example and without limitation, the supplementing engine 118 can receive a score from each computing engine 200 (e.g., indicating the relevance of the sampling objective 120 of the computing engine 200 to the machine learning model 114 and/or data sample set 106). The scores can indicate an improvement of each sampling objective 120 that could be achieved based on the selected data samples 124 for the data sampling criteria 122 of each computing engine 200. For example, the first computing engine 200-1 might have a low score due to the labels 110 being well-balanced, while the second computing engine 200-2 might have a high score due to the robustness of the machine learning model 114 being poor. The supplementing engine 118 can select the one or more data sampling criteria 122 based on a ranking of the scores received from each computing engine 200 (e.g., selecting the data sampling criteria 122 based on the highest-ranked computing engines 200).

In some embodiments, the supplementing engine 188 receives the sampling objective 120 from a user (e.g., based on a selection from a list of sampling objectives that could be applied to a data sample set associated with a machine learning model 114). Alternatively or additionally, in some embodiments, the supplementing engine 118 initially selects the sampling objective 120 from a sampling objective set of at least two sampling objectives 120. For example and without limitation, the supplementing engine 188 can score the machine learning model 114 for each of the at least two sampling objectives 120 of the sampling objective set (e.g., based on the scores of the computing engines 200), and select the sampling objective 120 based on the scores. In some embodiments, the supplementing engine 118 can score the machine learning model 114 by predicting an improvement of each sampling objective 120 that could be achieved based on a supplemented data sample set 128. can cause the data sampling criteria 122 and/or predicted improvement of the sampling objective 120 to be shown to the user.

In some embodiments, the supplementing engine 118 causes a determined sampling objective 120 to be displayed for a user (e.g., as an initial, suggested, and/or default sampling objective 120). In some such embodiments, the displayed sampling objective includes a predicted improvement of the sampling objective 120 based on the one or more data sampling criteria 122 (e.g., the degree with which representativeness could be improved). Based on receiving, from the user, an acceptance of the sampling objective 120, the supplementing engine 118 can select the data sampling criteria 122 (e.g., by invoking the computing engine 200 that is configured based on the sampling objective 120). Alternatively or additionally, the supplementing engine 118 might receive, from the user, an adjustment of the sampling objective 120 (e.g., a selection of a substitute sampling objective 120, and/or an additional sampling objective 120 that is to be pursued currently with the displayed sampling objective 120). In this case, the supplementing engine 188 determines the one or more data sampling criteria 122 based on the adjusted sampling objective 120.

In some embodiments, the supplementing engine 118 receives one or more data sampling criteria 122 from a user. For example and without limitation, the supplementing engine 118 might receive from the user an instruction to select, from the unlabeled data samples 116, additional data samples that might be associated with a selected label 110. Such instructions might reflect domain-specific knowledge of the user about the machine learning model 114, the data sample set 106, and/or the sampling objective 120. The supplementing engine 118 can combine the one or more data sampling criteria 122 received from the user with one or more selected data sampling criteria 122 (e.g., generated by a computing engine 200). Alternatively, the supplementing engine 118 can use the one or more data sampling criteria 122 received from the user instead of one or more selected data sampling criteria 122.

In some embodiments, the supplementing engine 118 determines, based on one or more sampling objectives 120, one or more additional steps to be taken while training or retraining the machine learning model 114. For example and without limitation, the supplementing engine 118 can determine that model imbalance could be improved by removing some data samples 108 from the data sample set 106 that are redundant and/or associated with an overrepresented label 110. The supplementing engine 118 can cause the additional steps can be shown to a user. Based on receiving an acceptance for the user, the supplementing engine 118 can apply the additional steps along with the one or more data sampling criteria 122 while training the machine learning model 114.

Figure 3:
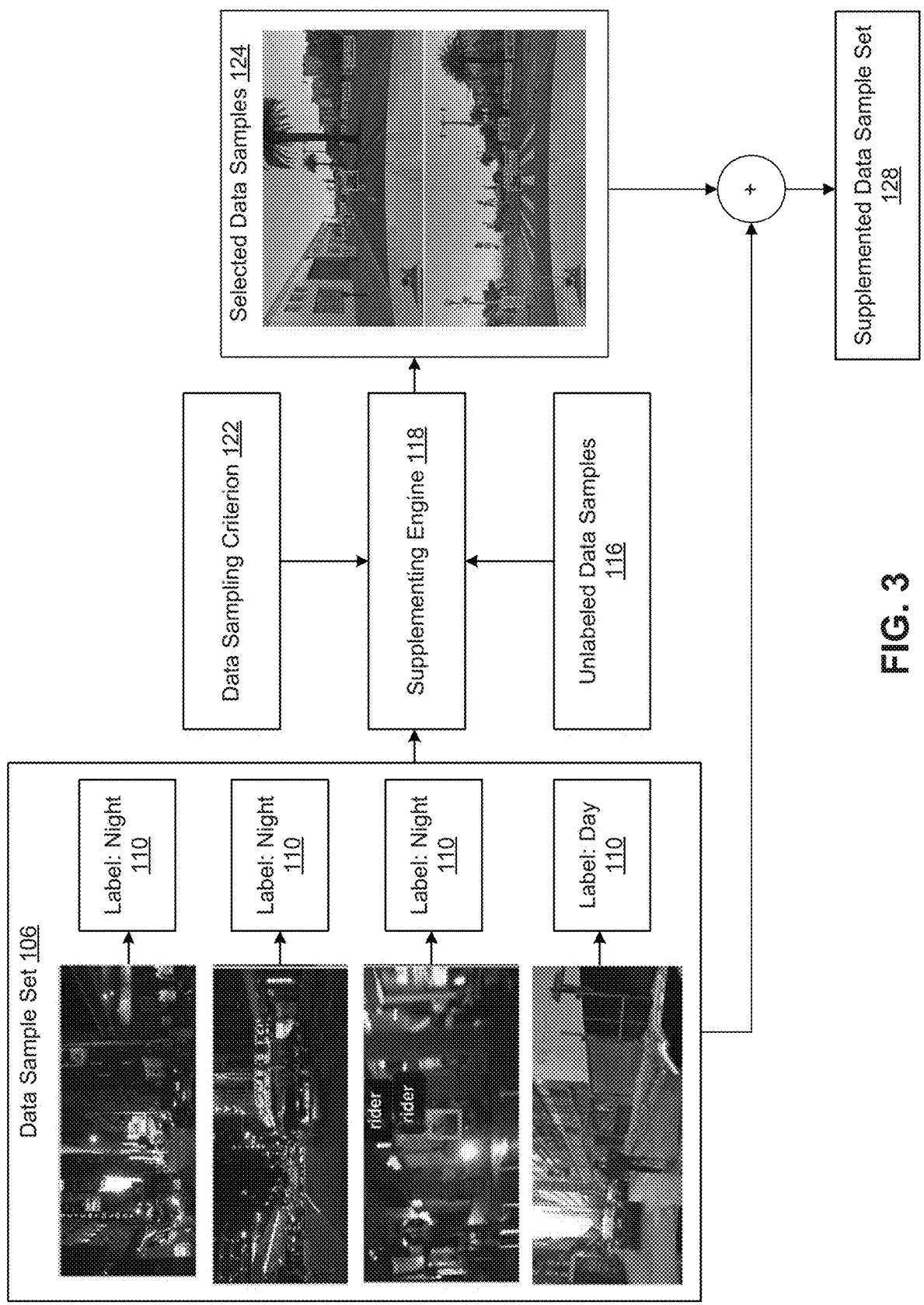
FIG. 3 is an illustration of a selection of data samples by the supplementing engine of FIG. 1 based on a first data sampling criterion, according to one or more embodiments.

FIG. 3 is an illustration of a selection of data samples 124 by the supplementing engine 118 of FIG. 1 based on a first data sampling criterion 122, according to one or more embodiments.

As shown, a data sample set 106 includes a set of data samples 108 representing images. Many images are associated with a first label 110 indicating images at night, while only a few images are associated with a second label 110 indicating images during the day. In order to address a sampling objective 120 of label imbalance, the data sampling criteria 122 specifies properties that indicate images during the day, such as a time range indicated by image EXIF metadata. The supplementing engine 118 applies the data sampling criterion 122 to the set of unlabeled data samples 116 and selects data samples 124 of images during the day. Adding the selected data samples 124 to the data sample set 106, along with labels 110 for such data samples 108, results in a supplemented data sample set 128 in which the data samples are balanced between the labels 110.

Figure 4:
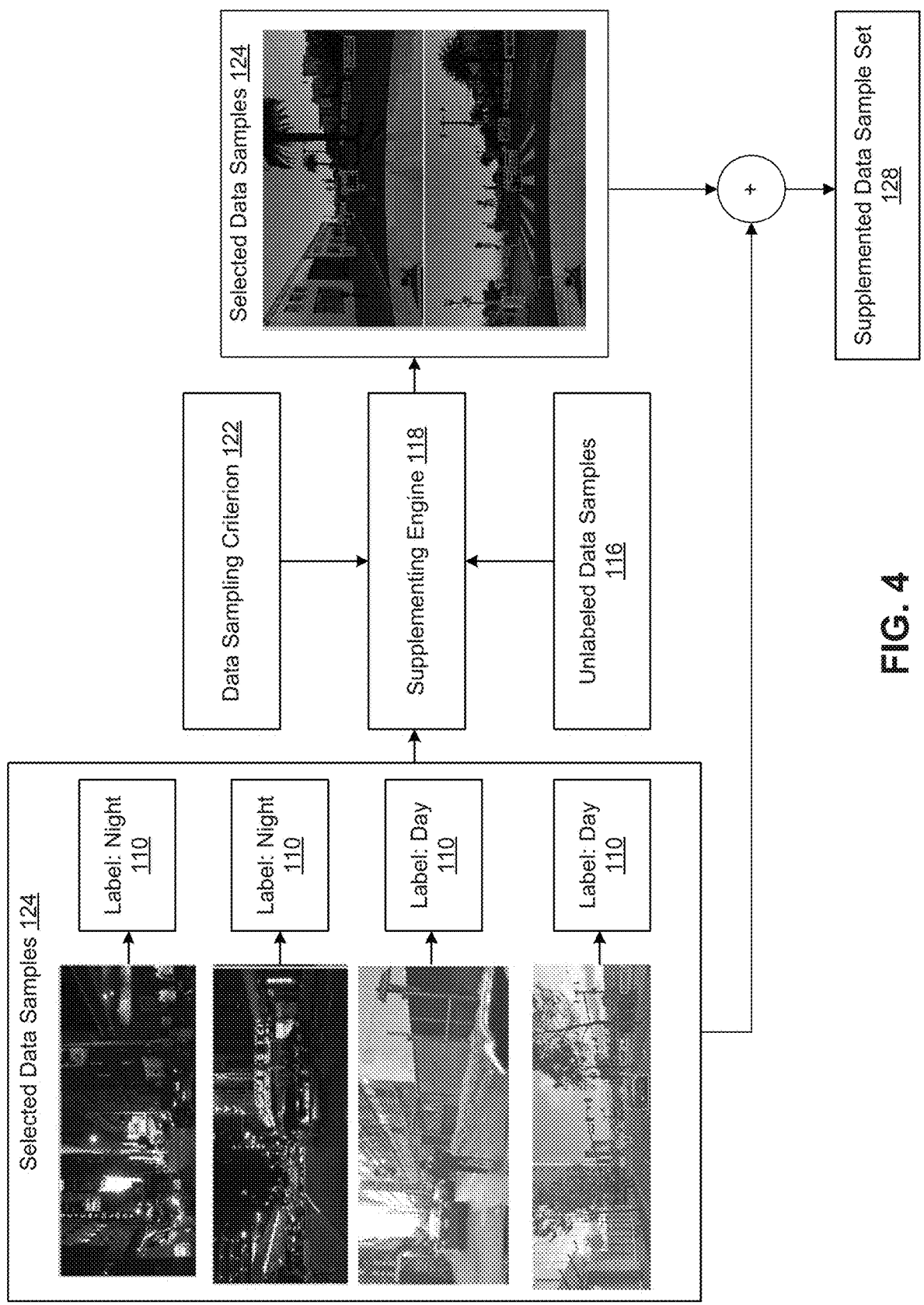
FIG. 4 is an illustration of a selection of data samples by the supplementing engine of FIG. 1 based on a second data sampling criterion, according to one or more embodiments.

FIG. 4 is an illustration of a selection of data samples by the supplementing engine of FIG. 1 based on a second data sampling criterion 122, according to one or more embodiments.

As shown, a data sample set 106 includes a set of data samples 108 representing images. The images associated with a first label 110 indicate images at night. These images were taken late at night and, as a result, have a very dark appearance. The images associated with a second label 110 indicate images during the day. These images were taken during midday and, as a result, have a very bright or light appearance. Due to the wide difference in brightness or lightness between the images at night and images during the day, the machine learning model exhibits poor performance for borderline images with a medium brightness or lightness, such as images taken at dusk. In order to address a sampling objective 120 of robustness, the data sampling criteria 122 indicates images with a medium brightness or lightness, such as images taken at dusk. That is, the machine learning model is unable to generalize a broader set of image features that represent images at night and images during the day. The supplementing engine 118 applies the data sampling criterion 122 to the set of unlabeled data samples 116 and selects data samples 124 of images taken at dusk. Adding the selected data samples 124 to the data sample set 106, along with a label 110 for the selected data samples 124, results in a supplemented data sample set 128 in which the machine learning model exhibits a more robust decision boundary between daytime and nighttime images.

In some embodiments, the supplementing engine 118 selects the least one data sample 124 from the unlabeled data samples 116 based on a prediction of the machine learning model 114 for the at least one data sample 124. As a first example and without limitation, the machine learning model 114 detects whether each image of an image-based set of unlabeled data samples 116 includes one or more object. The supplementing engine 118 can limit the selected data samples 124 to images in which the machine learning model 114 detects at least one object. As a second example and without limitation, the machine learning model 114 determines a confidence level for each data sample 108 of the data sample set 106. If the machine learning model 114 cannot determine a confidence level for a particular data sample 108 that is above a minimum confidence threshold, the supplementing engine 118 can include the data sample 108 to the set of selected data samples 124 to be labeled (e.g., to request a relabeling of the data sample 108).

In some embodiments, the supplementing engine 118 selects the at least one data sample 124 form the unlabeled data samples 116 by determining a score of the machine learning model 114 for each unlabeled data sample 116, and determining the selected data samples 124 based on the scores. For example, the supplementing engine 118 can predict a label 110 for each unlabeled data sample 116, and a score indicating a confidence in the correctness of each prediction. The supplementing engine 118 can determine, from among the unlabeled data samples 116, selected data samples 124 having a confidence above a minimum confidence (e.g., unlabeled data samples 116 that are likely to be associated with at least one label 110) and/or below a maximum confidence (e.g., unlabeled data samples 116 that are not definitely associated with at least one label 110).

In some embodiments, the supplementing engine 118 limits the data samples 124 from the unlabeled data samples 116 based on a selection threshold. As a first example and without limitation, the training of the machine learning model 114 can be constrained by a training budget (e.g., a maximum number of selected data samples 124 to be selected to train or retrain the machine learning model 114). As a second example and without limitation, the training of the machine learning model 114 can be constrained by an improvement threshold (e.g., a predicted degree of improvement of the sampling objective 120 of a data sample set 106 associated with the machine learning model 114 based on each selected data sample 124). The supplementing engine 118 can limit the selected data samples 124 based on the selection threshold. In some embodiments, the supplementing engine 118 can cause a suggested selection threshold to be displayed for a user (e.g., a maximum number of images to select from the unlabeled data samples 116). The supplementing engine 118 can use the suggested selection threshold based on receiving an acceptance of the suggested selection threshold from the user.

In some embodiments, the labeling engine 126 generates the supplemented data sample set 128 by adding the selected data samples 124 and associations with one or more labels 110 to the data sample set 106 for training or retraining of the machine learning model 114. In some other embodiments, the supplemented data sample set 128 includes only the selected data samples 124 and associated labels 110, and not the data samples 108 and labels 110 of the initial data sample set 106, for the training or retraining of the machine learning model 114.

In some embodiments, the machine learning trainer 112 continues or reinitiates training of an initially trained machine learning model 114 based on the supplemented data sample set 128. That is, the machine learning model 114 is initially partially or completely trained, and the machine learning trainer 112 continues or resumes the training of the machine learning model 114, which could improve the sampling objective 120. Alternatively or additionally, in some embodiments, the machine learning trainer 112 reinitializes the machine learning model 114, or generates a new machine learning model 114 with the same structure or a different structure, for training with the supplemented data sample set 128.

Figure 5:
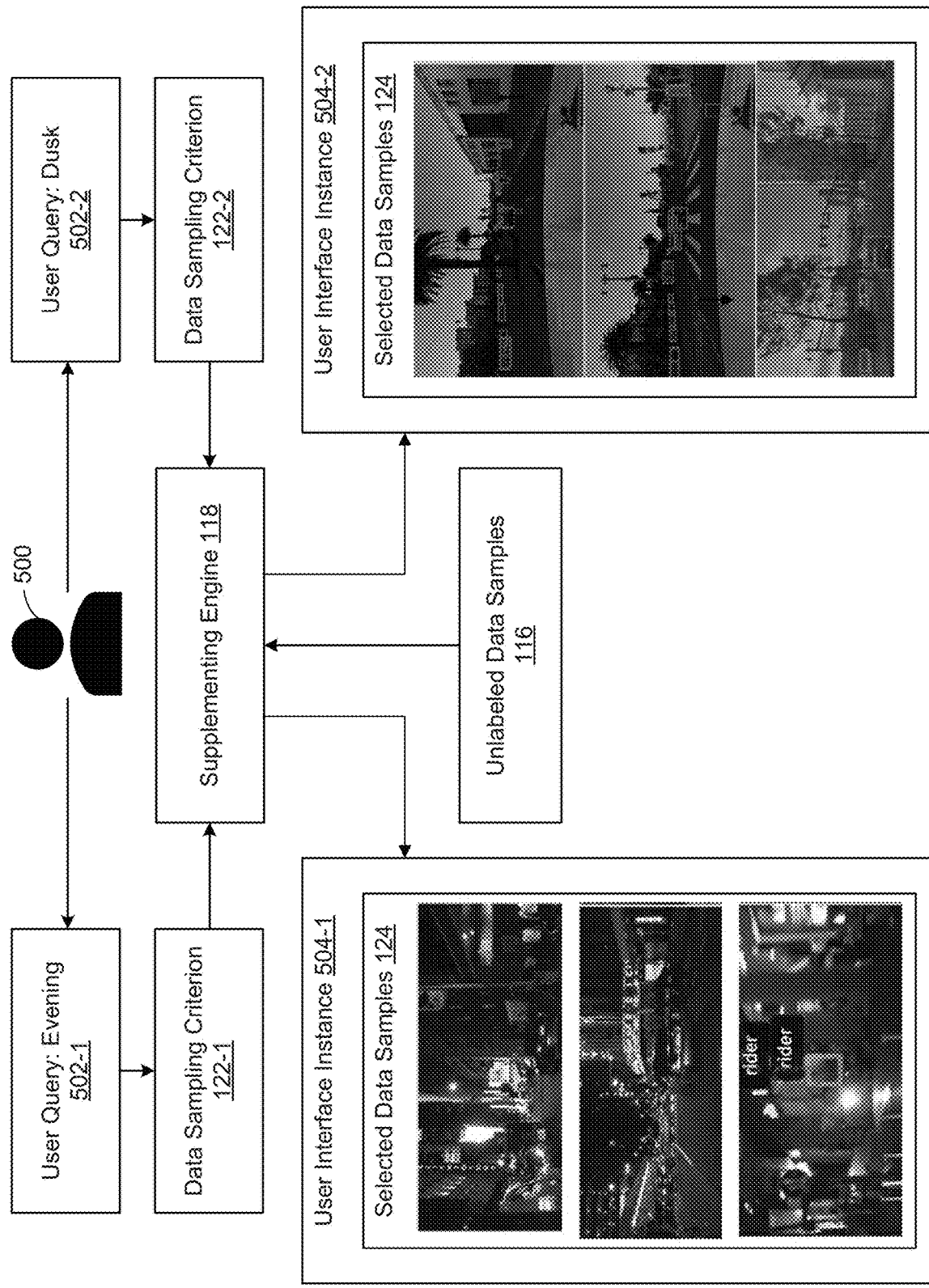
FIG. 5 is an illustration of a user interface for the selection of data samples shown in FIGS. 3 and 4, according to one or more embodiments.

FIG. 5 is an illustration of a user interface for the selection of data samples shown in FIGS. 3 and 4, according to one or more embodiments.

As shown, a user 500 submits a first user query 502-1 indicating a request to supplement the data sample set 106 with images taken during the evening. In formulating the first user query 502-1, the user 500 may submit the first user query 502-1 (e.g., as a natural-language query) based on a sampling objective 120, e.g., an interest in improving label robustness by labeling more images captured earlier in the evening, rather than late at night. Alternatively, in formulating the first user query 502-2, the user 500 may submit the first user query 502-2 as a data sampling criterion 122, e.g., a request to supplement the data sample set 106 with additional images that are associated with the label "evening."

Based on the first user query 502-1, the supplementing engine 118 analyzes the set of unlabeled data samples 116. The supplementing engine 118 evaluates the first user query 502-1 in order to determine the sampling objective 120 intended by the user 500, and based on the sampling objective 120, the supplementing engine 118 can determine one or more data sampling criteria 122-1. Alternatively, the supplementing engine 118 determines one or more sampling criteria 122-1 indicated by the first user query 502-1 (e.g., as indicative features of images that are associated with the term "evening"). The supplementing engine 118 selects, from the set of unlabeled data samples 116, selected data samples 124 based on the one or more sampling criteria 122-1. The supplementing engine 118 displays for the user 500 a first user interface instance 504-1 that shows the selected data samples 124 that were selected in response to the first user query 502-1.

The user 500 reviews the selected data samples 124 and determines that the selected data samples 124 that were identified for the first user query 502-1 of "evening" are not sufficient to achieve the sampling objective 120, because they are too similar to data samples 108 of the data sample set 106 that are associated with the "night" label 110. The user 500 reconsiders the user query 502 in order to request images earlier in the evening, such as dusk. The user 500 submits a second user query 502-2 that instead indicates a request to supplement the data sample set 106 with images taken at dusk. As previously discussed, the user 500 could submit the second user query 502-2 (e.g., as a natural-language query) based on a sampling objective 120, or as a data sampling criterion 122.

Based on the second user query 502-2, the supplementing engine 118 evaluates the second user query 502-2 in order to determine the sampling objective 120 intended by the user 500, and based on the sampling objective 120, the supplementing engine 118 can determine one or more data sampling criteria 122-2. Alternatively, the supplementing engine 118 determines one or more sampling criteria 122-2 indicated by the second user query 502-2 (e.g., as indicative features of images that are associated with the term "dusk"). The supplementing engine 118 selects, from the set of unlabeled data samples 116, selected data samples 124 based on the one or more sampling criteria 122-2. The supplementing engine 118 displays for the user 500 a second user interface instance 504-2 that shows the selected data samples 124 that were selected in response to the second user query 502-2.

The user 500 reviews the selected data samples 124 in response to the second user query 502-2. The user 500 determines that these selected data samples 124 satisfy the sampling objective 120 and/or data sampling criteria 122-2. The user 500 indicates that the selected data samples 124 are satisfactory, such as by clicking on a "Done" button. By presenting the user interface instances 504, the supplementing engine 118 involves the user 500 in realtime in the curation of the data sample set 106 by supplementing with the selected data samples 124.

Based upon the indication of the completion of selecting the selected data samples 124, the labeling engine 126 initiates labeling of the selected data samples 124. For example and without limitation, a labeling engine 126 can display each selected data sample 124 to the user 500 and receive, from the user 500, a selection of a label 110 to be associated the selected data sample 124. Alternatively or additionally, the labeling engine 126 can also predict a label 110 for each selected data sample 124 and show the predicted label 110 to the user 500 for confirmation and/or correction.

Figure 6:
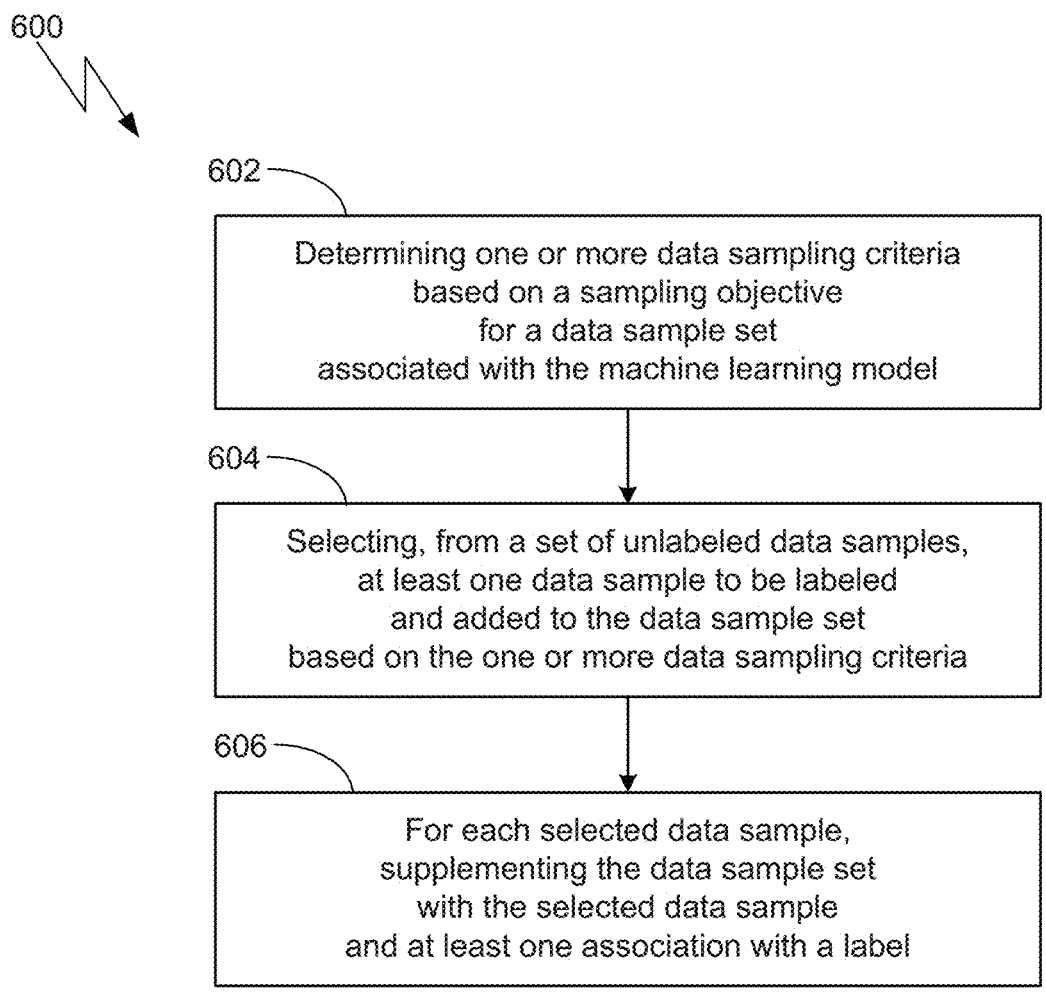
FIG. 6 is a flow diagram of method steps for curating a data sample set, according to one or more embodiments.

FIG. 6 is a flow diagram of method steps for curating a data sample set, according to one or more embodiments. Although the method steps are described with reference to FIGS. 1-5, persons skilled in the art will understand that any system may be configured to implement the method steps, in any order, in other embodiments.

As shown, at step 602, a supplementing engine 118 determines one or more data sampling criteria based on a sampling objective for the data sample set associated with a machine learning model. The determining can be based, for example, on sampling objectives that are received from a user, or a suggested set of sampling objectives that are approved and/or adjusted by a user. In some embodiments, the one or more data sampling criteria are determined by one or more computing engines, each computing engine being configured to evaluate the sampling objective and generate one or more data sampling criteria.

At step 604, the supplementing engine 118 selects, from a set of unlabeled data samples, at least one data sample to be labeled and added to a data sample set associated with the machine learning model based on the one or more data sampling criteria. In some embodiments, the supplementing engine 118 selects the data samples based on predictions of a machine learning model, and/or based on scores of each data sampling criterion for each data sample in the set of unlabeled data samples. In some embodiments, the supplementing engine 118 limits the selected data samples based on a selection threshold, such as (without limitation) a sampling budget.

At step 606, for each selected data sample, a labeling engine 126 supplements the data sample set with the selected data sample and at least one association with a label. In some embodiments, the selected data samples are represented to a user, and one or more labels selected by a user are associated with the selected data samples.

In sum, techniques are disclosed for automatic data curation. A supplementing engine receives a sampling objective for a data sample set associated with a machine learning model, such as improving label balance, improving robustness, or improving consistency. Based on the sampling objective, the supplementing engine determines data sampling criteria for selecting samples from the unlabeled data sample set for labeling to supplement the data sample set. The data sampling criteria indicate properties of data samples that could supplement a data sample set, which could improve the sampling objective for the data sample set associated with the machine learning model. Based on the data sampling criteria, the supplementing engine selects, from a set of unlabeled data samples, data samples to be labeled and added to the data sample set. The selected data samples and associated labels are added to the data sample set. Training or retraining the machine learning model using the supplemented data sample set satisfies the sampling objective for the data sample set associated with the machine learning model.

At least one technical advantage of the disclosed techniques is the data sample set is supplemented to include additional data samples that can improve the sampling objective for a data sample set associated with the machine learning model, such as (without limitation) improving label balance, improving robustness, and/or improving consistency. Machine learning models that are trained or retrained on the refined data sample set can exhibit improved performance such as labeling accuracy, precision, and/or recall. Further, supplementing the data sample set with data samples based on an indicated set of objectives for improving machine learning models can increase the likelihood of successful training while reducing cost and complexity. Finally, allowing a developer to indicate objectives for improved machine learning models, and selecting unlabeled data samples for labeling based on the indicated objectives, increases the performance of machine learning models trained on the supplemented data sample set even if the developer does not understand the causes of poor performance.

1. In some embodiments, a computer-implemented method for curating a data sample set comprises determining one or more data sampling criteria based on a sampling objective for the data sample set associated with a machine learning model; selecting, from a set of unlabeled data samples, at least one data sample to be labeled and added to the data sample set based on the one or more data sampling criteria; and for each selected data sample, supplementing the data sample set with the selected data sample and at least one association with a label.

2. The method of clause 1, further comprising determining the sampling objective based on at least one of the data sample set or the machine learning model.

3. The method of clauses 1 or 2, further comprising determining the sampling objective based on predictions of the machine learning model for at least one data sample of the data sample set.

4. The method of any of clauses 1-3, wherein the predictions of the machine learning model for the at least one data sample include a class probability distribution for each label of the data sample set.

5. The method of any of clauses 1-4, wherein the sampling objective is selected from a sampling objective set, and further comprising, for each sampling objective included in the sampling objective set, generating corresponding data sampling criteria via a different computing engine in a set of computing engines.

6. The method of clause 5, wherein at least one computing engine in the set of computing engine is associated with a domain of the data sample set.

7. The method of clauses 5 or 6, wherein determining the one or more data sampling criteria comprises receiving a score from each computing engine, and selecting the one or more data sampling criteria based on a ranking of the scores received from the set of computing engines.

8. In some embodiments, one or more non-transitory computer readable media store instructions that, when executed by one or more processors, cause the one or more processors to perform the steps of determining one or more data sampling criteria based on a sampling objective for a data sample set associated with a machine learning model; selecting, from a set of unlabeled data samples, at least one data sample to be labeled and added to the data sample set based on the one or more data sampling criteria; and for each selected data sample, supplementing the data sample set with the selected data sample and at least one association with a label.

9. The one or more non-transitory computer readable media of clause 8, wherein the sampling objective is a label balance sampling objective, and the one or more sampling criteria indicate unlabeled data samples for which the machine learning model predicts a label that is underrepresented in the data sample set.

10. The one or more non-transitory computer readable media of clauses 8 or 9, wherein the sampling objective is a robustness sampling objective, and the one or more sampling criteria indicate unlabeled data samples for which the machine learning model predicts a label, and that are different than labeled data samples that are associated with the label.

11. The one or more non-transitory computer readable media of any of clauses 8-10, wherein the sampling objective is a consistency sampling objective, and the one or more sampling criteria indicate unlabeled data samples for which the machine learning model predicts at least two labels with confidence scores for which a difference is within a confidence score difference threshold.

12. The one or more non-transitory computer readable media of any of clauses 8-11, further comprising selecting the sampling objective from a sampling objective set of at least two sampling objectives.

13 The one or more non-transitory computer readable media of clause 12, further comprising: scoring the machine learning model for each of the at least two sampling objectives of the sampling objective set, and selecting the sampling objective based on the scores.

14. The one or more non-transitory computer readable media of clause 13, wherein scoring the machine learning model includes predicting an improvement of each sampling objective.

15. The one or more non-transitory computer readable media of any of clauses 12-14, further comprising: causing the sampling objective to be displayed for a user, and receiving, from the user, an acceptance of the sampling objective.

16. The one or more non-transitory computer readable media of claim 15, wherein the displayed sampling objective includes a predicted improvement of the sampling objective based on the one or more data sampling criteria.

17. The one or more non-transitory computer readable media of any of clauses 8-16, further comprising: receiving, from a user, an adjustment of the sampling objective, and determining the one or more data sampling criteria based on the adjusted sampling objective.

18. The one or more non-transitory computer readable media of any of clauses 8-17, wherein determining the one or more data sampling criteria includes receiving one or more of the one or more data sampling criteria from a user.

19. The one or more non-transitory computer readable media of any of clauses 8-18, wherein selecting the at least one data sample is based on a prediction of the machine learning model for the at least one data sample.

20. The one or more non-transitory computer readable media of any of clauses 8-19, wherein selecting the at least one data sample includes determining a score of the machine learning model for each unlabeled data sample, and selecting the at least one data sample based on the scores.

21. The one or more non-transitory computer readable media of any of clauses 8-20, wherein selecting the data samples includes limiting the selected data samples based on a selection threshold.

22. The one or more non-transitory computer readable media of clause 21, further comprising: causing a suggested selection threshold to be displayed for a user, and receiving, from the user, an acceptance of the suggested selection threshold.

23. In some embodiments, a system comprises a memory that stores instructions, and a processor that is coupled to the memory and, when executing the instructions, is configured to determine one or more data sampling criteria based on a sampling objective for a data sample set associated with a machine learning model; select, from a set of unlabeled data samples, at least one data sample to be labeled and added to the data sample set based on the one or more data sampling criteria; and for each selected data sample, supplement the data sample set with the selected data sample and at least one association with a label.

Any and all combinations of any of the claim elements recited in any of the claims and/or any elements described in this application, in any fashion, fall within the contemplated scope of the present invention and protection.

The descriptions of the various embodiments have been presented for purposes of illustration, but are not intended to be exhaustive or limited to the embodiments disclosed. Many modifications and variations will be apparent to those of ordinary skill in the art without departing from the scope and spirit of the described embodiments.

Aspects of the present embodiments may be embodied as a system, method or computer program product. Accordingly, aspects of the present disclosure may take the form of an entirely hardware embodiment, an entirely software embodiment (including firmware, resident software, microcode, etc.) or an embodiment combining software and hardware aspects that may all generally be referred to herein as a "module," a "system," or a "computer." In addition, any hardware and/or software technique, process, function, component, engine, module, or system described in the present disclosure may be implemented as a circuit or set of circuits. Furthermore, aspects of the present disclosure may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

Aspects of the present disclosure are described above with reference to flowchart illustrations and/or block diagrams of methods, apparatus (systems) and computer program products according to embodiments of the disclosure. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine. The instructions, when executed via the processor of the computer or other programmable data processing apparatus, enable the implementation of the functions/acts specified in the flowchart and/or block diagram block or blocks. Such processors may be, without limitation, general purpose processors, special-purpose processors, application-specific processors, or field-programmable gate arrays.

The flowchart and block diagrams in the figures illustrate the architecture, functionality, and operation of possible implementations of systems, methods and computer program products according to various embodiments of the present disclosure. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

While the preceding is directed to embodiments of the present disclosure, other and further embodiments of the disclosure may be devised without departing from the basic scope thereof, and the scope thereof is determined by the claims that follow.

What is claimed is:

1. A computer-implemented method for curating a data sample set, the method comprising:
    generating a set of outputs by processing at least one data sample using a trained machine learning model;
    concurrently determining on a plurality of computing instances a plurality of relevance scores between a plurality of sampling objectives and the set of outputs generated using the trained machine learning model, wherein each sampling objective in the plurality of sampling objectives is associated with a different computing instance in the plurality of computing instances and is associated with a different objective that is to be achieved during retraining of the trained machine learning model, and wherein each relevance score represents a relevance of a given sampling objective in the plurality of sampling objectives to the trained machine learning model;
    determining a given sampling objective for the data sample set that is to be achieved during retraining of the trained machine learning model, wherein the determining of the given sampling objective is based on the plurality of relevance scores;
    determining one or more data sampling criteria based on the given sampling objective;
    selecting, from a set of unlabeled data samples, at least one data sample for labeling and adding to the data sample set based on the one or more data sampling criteria;

for each selected data sample, supplementing the data sample set with the selected data sample and at least one association with a label; and retraining the trained machine learning model using the supplemented data sample set.

2. The method of claim 1, wherein the given sampling objective is further determined based on the data sample set.

3. The method of claim 1, wherein the set of outputs of the trained machine learning model for the at least one data sample include a class probability distribution for each label of the data sample set.

4. The method of claim 1, wherein at least one computing instance in the plurality of computing instances associated with a domain of the data sample set.

5. One or more non-transitory computer readable media storing instructions that, when executed by one or more processors, cause the one or more processors to perform the steps of:

generating a set of outputs by processing at least one data sample using a trained machine learning model;

concurrently determining on a plurality of computing instances a plurality of relevance scores between a plurality of sampling objectives and the set of outputs generated using the trained machine learning model, wherein each sampling objective in the plurality of sampling objectives is associated with a different computing instance in the plurality of computing instances and is associated with a different objective that is to be achieved during retraining of the trained machine learning model, and wherein each relevance score represents a relevance of a given sampling objective in the plurality of sampling objectives to the trained machine learning model;

determining a given sampling objective for the data sample set that is to be achieved during retraining of the trained machine learning model, wherein the determining of the given sampling objective is based on the plurality of relevance scores;

determining one or more data sampling criteria based on the given sampling objective;

selecting, from a set of unlabeled data samples, at least one data sample for labeling and adding to the data sample set based on the one or more data sampling criteria;

for each selected data sample, supplementing the data sample set with the selected data sample and at least one association with a label; and retraining the trained machine learning model using the supplemented data sample set.

6. The one or more non-transitory computer readable media of claim 5, wherein the sampling objective is a label balance sampling objective, and the one or more sampling criteria indicate unlabeled data samples for which the trained machine learning model predicts a label that is underrepresented in the data sample set.

7. The one or more non-transitory computer readable media of claim 5, wherein the sampling objective is a robustness sampling objective, and the one or more sampling criteria indicate unlabeled data samples for which the trained machine learning model predicts a label, and that are different than labeled data samples that are associated with the label.

8. The one or more non-transitory computer readable media of claim 5, wherein the sampling objective is a consistency sampling objective, and the one or more sampling criteria indicate unlabeled data samples for which the trained machine learning model predicts at least two labels with confidence scores for which a difference is within a confidence score difference threshold.

9. The one or more non-transitory computer readable media of claim 5, wherein the instructions, when executed by the one or more processors, further cause the one or more processors to perform the steps of:

causing the given sampling objective to be displayed for a user, and receiving, from the user, an acceptance of the given sampling objective.

10. The one or more non-transitory computer readable media of claim 9, wherein the displayed sampling objective includes a predicted improvement of the sampling objective based on the one or more data sampling criteria.

11. The one or more non-transitory computer readable media of claim 5, wherein the instructions, when executed by the one or more processors, further cause the one or more processors to perform the steps of:

receiving, from a user, an adjustment of the given sampling objective, and determining the one or more data sampling criteria based on the adjusted sampling objective.

12. The one or more non-transitory computer readable media of claim 5, wherein determining the one or more data sampling criteria includes receiving one or more of the one or more data sampling criteria from a user.

13. The one or more non-transitory computer readable media of claim 5, wherein selecting the data samples includes limiting the selected data samples based on a selection threshold.

14. The one or more non-transitory computer readable media of claim 13, wherein the instructions, when executed by the one or more processors, further cause the one or more processors to perform the steps of:

causing a suggested selection threshold to be displayed for a user, and receiving, from the user, an acceptance of the suggested selection threshold.

15. A system, comprising:

a memory that stores instructions, and a processor that is coupled to the memory and, when executing the instructions, is configured to:

generate a set of outputs by processing at least one data sample using a trained machine learning model;

concurrently determine on a plurality of computing instances a plurality of relevance scores between a plurality of sampling objectives and the set of outputs generated using the trained machine learning model, wherein each sampling objective in the plurality of sampling objectives is associated with a different computing instance in the plurality of computing instances and is associated with a different objective that is to be achieved during retraining of the trained machine learning model, and wherein each relevance score represents a relevance of a given sampling objective in the plurality of sampling objectives to the trained machine learning model;

determine a given sampling objective for the data sample set that is to be achieved during retraining of the trained machine learning model, wherein the determining of the given sampling objective is based on the plurality of relevance scores;

determine one or more data sampling criteria based on the given sampling objective;

select, from a set of unlabeled data samples, at least one data sample for labeling and adding to the data sample set based on the one or more data sampling criteria;

for each selected data sample, supplement the data sample set with the selected data sample and at least one association with a label; and retraining the trained machine learning model using the supplemented data sample set.

* * * * *

UNITED STATES PATENT AND TRADEMARK OFFICE
CERTIFICATE OF CORRECTION

PATENT NO. : 12,271,443 B1
APPLICATION NO. : 17/482860
DATED : April 8, 2025
INVENTOR(S) : Diego Ardila et al.

Page 1 of 1

It is certified that error appears in the above-identified patent and that said Letters Patent is hereby corrected as shown below:

In the Claims

In Column 21, Line 13, in Claim 4, delete "associated" and insert -- is associated --.

In Column 23, Line 8, in Claim 15, delete "retraining" and insert -- retrain --.

Signed and Sealed this
Twelfth Day of August, 2025

Coke Morgan Stewart
*Acting Director of the United States Patent and Trademark Office*